(12) United States Patent
Lin et al.

(10) Patent No.: US 11,071,711 B2
(45) Date of Patent: Jul. 27, 2021

(54) COMPOSITIONS FOR SKIN APPLICATION

(71) Applicants: Yi-Chun Lin, Jersey City, NJ (US);
Marc Cornell, Jackson, NJ (US);
Gregory Bays Brown, Louisville, KY
(US); Elizabeth Myra Martin,
Stamford, CT (US)

(72) Inventors: Yi-Chun Lin, Jersey City, NJ (US);
Marc Cornell, Jackson, NJ (US);
Gregory Bays Brown, Louisville, KY
(US); Elizabeth Myra Martin,
Stamford, CT (US)

( * ) Notice: Subject to any disclaimer, the term of this patent is extended or adjusted under 35 U.S.C. 154(b) by 169 days.

(21) Appl. No.: 16/513,517

(22) Filed: Jul. 16, 2019

(65) Prior Publication Data

US 2020/0078292 A1   Mar. 12, 2020

Related U.S. Application Data

(63) Continuation of application No. 15/593,509, filed on May 12, 2017, now abandoned.

(60) Provisional application No. 62/335,918, filed on May 13, 2016.

(51) Int. Cl.
| | |
|---|---|
| *A61K 8/99* | (2017.01) |
| *A61K 8/49* | (2006.01) |
| *A61K 8/60* | (2006.01) |
| *A61K 8/64* | (2006.01) |
| *A61Q 19/08* | (2006.01) |
| *A61K 8/72* | (2006.01) |

(52) U.S. Cl.
CPC ............... *A61K 8/99* (2013.01); *A61K 8/498* (2013.01); *A61K 8/4946* (2013.01); *A61K 8/606* (2013.01); *A61K 8/64* (2013.01); *A61K 8/72* (2013.01); *A61Q 19/08* (2013.01); *A61K 2800/28* (2013.01); *A61K 2800/74* (2013.01); *A61K 2800/85* (2013.01)

(58) Field of Classification Search
None
See application file for complete search history.

(56) References Cited

U.S. PATENT DOCUMENTS

| | | |
|---|---|---|
| 6,180,662 B1 | 1/2001 | Lanzendorfer et al. |
| 8,569,358 B2 | 10/2013 | Bernard et al. |
| 9,050,477 B2 | 6/2015 | Fournial et al. |
| 9,089,505 B1 | 7/2015 | Saxena et al. |
| 9,693,947 B1 | 7/2017 | Marini et al. |
| 2004/0014814 A1 | 1/2004 | Grigg et al. |
| 2004/0086526 A1 | 5/2004 | Danoux et al. |
| 2004/0115766 A1 | 6/2004 | Lintner |
| 2006/0233738 A1 | 10/2006 | Miyata et al. |
| 2006/0286046 A1 | 12/2006 | Haber |
| 2012/0028916 A1 | 2/2012 | Fournial et al. |
| 2014/0349947 A1 | 11/2014 | Odintsov |
| 2015/0359734 A1 | 12/2015 | Boland et al. |

FOREIGN PATENT DOCUMENTS

| | | |
|---|---|---|
| CN | 104382833 A | 3/2015 |
| EP | 1902756 A1 | 3/2008 |
| WO | 02066668 A2 | 8/2002 |
| WO | 2007042495 A1 | 4/2007 |
| WO | 20140170801 A1 | 10/2014 |
| WO | 2016012973 A1 | 1/2016 |

OTHER PUBLICATIONS

International Search Report and Written Opinion for International (PCT) Application No. PCT/US2017/032334 dated Aug. 8, 2017. (12 pages).
Gazak, Radek et al., "Silybin and Silymarin—New and Emerging Applications in Medicine", Current Medicinal Chemistry, 2007, vol. 14, No. 3, 315-338. (24 pages).
Venuceane™ brochure by Sederma (copyright 2007-2012). (2 pages).
Kitajima, Seiji et al., "Silybin from Silybum Marianum Seeds Inhibits Confluent-Induced Keratinocytes Differentiation as Effectively as Retinoic Acid without Inducing Inflammatory Cytokine", Journal of Clinical Biochemistry and Nutrition, vol. 45, Sep. 2009, 178-84. (7 pages).
Garrod, David et al., "Desmosome structure, composition and function", Biochimica et Biophysica Acta 1778, 2008, 572-587. (16 pages).
International Preliminary Report on Patentability for International (PCT) Application No. PCT/US2017/032334 dated Nov. 22, 2018. (9 pages).
Singh, Rana P. et al., "Cosmeceuticals and Silibinin," Clin Dermatol, 2009, 27(5), 479-484. (9 pages).

*Primary Examiner* — David W Berke-Schlessel
(74) *Attorney, Agent, or Firm* — Lewis Roca Rothgerber Christie LLP

(57) ABSTRACT

Skin care compositions are provided which contain *Thermus thermophilus* ferment and silybin and provide anti-aging and reparative effect for skin. The compositions may also include one or more additional substances selected from carnosine, adenosine and CG-EDP3. The substances are dispersed in an aqueous carrier, such as water, to be applied to the skin in a spreadable form.

14 Claims, 3 Drawing Sheets

FIGURE 1

| Subject No. | | Day | | | | | | | | | | | | | | | | | | | |
|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 |
| 1 | TP | 3 | 3 | 3 | 2.5 | 2 | 1 | 1 | 1 | 0.5 | 0 | NR | NR | NR | NR | NR | NR | NR | NR | NR | NR |
| | C | 3 | 3 | 3 | 3 | 3 | 2.5 | 2.5 | 2.5 | 2.5 | 2 | 1.5 | 1 | 0.5 | 0.5 | 0.5 | 0 | NR | NR | NR | NR |
| 2 | TP | 3 | 3 | 3 | 2.5 | 2.5 | 1 | 1 | 1 | 0.5 | 0 | NR | NR | NR | NR | NR | NR | 1 | NR | NR | NR |
| | C | 3 | 3 | 3 | 3 | 3 | 2.5 | 2.5 | 2.5 | 2.5 | 2 | 2 | 2 | 1 | 1 | 1 | 1 | 0.5 | 0 | NR | NR |
| 3 | TP | 3 | 3 | 3 | 2.5 | 2 | 1 | 1 | 1 | 0.5 | 0 | NR | NR | NR | NR | NR | NR | 0.5 | 0 | NR | NR |
| | C | 3 | 3 | 3 | 3 | 3 | 2.5 | 2.5 | 2.5 | 2.5 | 2 | 2 | 1.5 | 1 | 1 | 1 | 0.5 | 0 | NR | NR | NR |
| 4 | TP | 3 | 2.5 | 2 | 2 | 1.5 | 0.5 | 0.5 | 0.5 | 0 | NR | 0 | NR | NR | NR | NR | NR | NR | NR | NR | NR |
| | C | 3 | 3 | 3 | 3 | 2.5 | 2 | 2 | 2 | 2 | 2 | 1.5 | 1.5 | 1 | 1 | 1 | 0.5 | 0 | NR | NR | NR |
| 5 | TP | 3 | 3 | 3 | 2.5 | 2 | 1 | 1 | 1 | 1 | 0.5 | 0 | NR | NR | NR | NR | NR | 0 | NR | NR | NR |
| | C | 3 | 3 | 3 | 3 | 3 | 2.5 | 2.5 | 2.5 | 2 | 2 | 1.5 | 1.5 | 1 | 1 | 1 | 0.5 | 0 | NR | NR | NR |
| 6 | TP | 3 | 3 | 2.5 | 2 | 1.5 | 0 | 0 | 0 | NR | NR | NR | 1 | NR | NR | NR | NR | NR | NR | NR | NR |
| | C | 32 | 3 | 3 | 3 | 3 | 2.5 | 2.5 | 2.5 | 2 | 2 | 1.5 | 0.5 | 0.5 | 0.5 | 0.5 | 0 | NR | NR | NR | NR |
| 7 | TP | 2 | 2 | 1.5 | 1.5 | 1 | 0.5 | 0.5 | 0.5 | 0 | 1 | 1 | 0.5 | 0 | 0 | 0 | 0 | NR | NR | NR | NR |
| | C | 2 | 2 | 2 | 2 | 2 | 1.5 | 1.5 | 1.5 | 1.5 | NR | NR | NR | NR | NR | NR | NR | NR | NR | NR | NR |
| 8 | TP | 2 | 2 | 1.5 | 1.5 | 1 | 0.5 | 0.5 | 0.5 | 0 | 1 | 0.5 | 0 | NR | NR | NR | NR | NR | NR | NR | NR |
| | C | 2 | 2 | 2 | 2 | 2 | 1.5 | 1.5 | 1.5 | 1 | 1 | 0.5 | 0 | NR | NR | NR | NR | NR | NR | NR | NR |
| 9 | TP | 3 | 3 | 3 | 2.5 | 2.5 | 1.5 | 1.5 | 1.5 | 1 | 2 | 2 | 1.5 | NR | 1 | 1 | 0.5 | NR | NR | NR | NR |
| | C | 3 | 3 | 3 | 3 | 3 | 3 | 3 | 3 | 2.5 | 0.5 | 0 | 0 | NR | NR | NR | NR | NR | NR | NR | NR |
| 10 | TP | 3 | 3 | 3 | 2.5 | 2.5 | 1 | 1 | 1 | 1 | 2 | 0 | 1.5 | NR | 1 | 1 | 0 | 0 | NR | NR | NR |
| | C | 3 | 3 | 3 | 3 | 3 | 3 | 3 | 3 | 2.5. | 0.5 | 1.5 | 1.5 | 0.5 | 0.5 | 0.5 | 0.5 | NR | NR | NR | NR |
| 11 | TP | 3 | 3 | 3 | 2 | 2 | 1 | 1 | 1 | 1 | 2 | NR | 1.5 | NR | NR | NR | NR | NR | NR | NR | NR |
| | C | 3 | 3 | 3 | 3 | 3 | 3 | 3 | 3 | 0.5 | 0 | 2 | 1.5 | 1 | 1 | 1 | 0.5 | 0 | NR | NR | NR |
| 12 | TP | 3 | 3 | 2.5 | 2 | 1.5 | 0.5 | 0.5 | 0.5 | 0 | NR | 2 | 1.5 | 1 | 1 | 1 | 0.5 | 0 | NR | NR | NR |
| | C | 3 | 3 | 3 | 3 | 3 | 3 | 3 | 3 | 2.5 | 2 | 2 | NR | NR | NR | NR | NR | NR | NR | NR | NR |
| 13 | TP | 3 | 3 | 3 | 3 | 2.5 | 1.5 | 1.5 | 1.5 | 1 | 1 | 0.5 | 0 | NR | 1 | 1 | 1 | 0 | NR | NR | NR |
| | C | 3 | 3 | 3 | 3 | 3 | 3 | 3 | 3 | 3 | 2.5 | 2.5 | 2 | 1 | 1 | 1 | 0.5 | 0 | NR | NR | NR |
| 14 | TP | 2 | 2 | 2 | 1.5 | 1 | 0.5 | 0.5 | 0.5 | 0 | NR | NR | NR | NR | NR | NR | NR | NR | NR | NR | NR |

FIGURE 1 (CONT)

| | | | | | | | | | | | | | | | | | | | | | | |
|---|---|---|---|---|---|---|---|---|---|---|---|---|---|---|---|---|---|---|---|---|---|---|
| 15 | C | 2 | 2 | 2 | 2 | 2 | 1.5 | 1.5 | 1.5 | 1.5 | 1 | 1 | 0.5 | 1 | 0 | 0 | 0 | 0 | NR | NR | NR |
| | TP | 3 | 3 | 2.5 | 2.5 | 3 | 1 | 1 | 1 | 0.5 | 0 | 0 | NR | NR | NR | NR | NR | NR | NR | NR | NR |
| 16 | C | 3 | 3 | 3 | 3 | 3 | 3 | 3 | 3 | 3 | 2.5 | 2.5 | 2 | 1 | 1 | 1 | 1 | 0.5 | 0 | NR | NR |
| | TP | 3 | 3 | 3 | 3 | 2.5 | 1.5 | 1.5 | 1.5 | 1 | 1 | 0.5 | 0 | 0.5 | NR | NR | NR | NR | NR | NR | NR |
| 17 | C | 3 | 3 | 3 | 3 | 3 | 3 | 3 | 3 | 3 | 3 | 2.5 | 2 | 2.5 | 1 | 1 | 1 | 0.5 | 0.5 | NR | NR |
| | TP | 3 | 3 | 3 | 3 | 2 | 0.5 | 0.5 | 0.5 | 0.5 | 0 | NR | NR | NR | NR | NR | NR | NR | NR | NR | NR |
| 18 | C | 3 | 3 | 3 | 3 | 3 | 3 | 3 | 3 | 3 | 2.5 | 2 | 2 | 2 | 1 | 1 | 1 | 0.5 | 0.5 | NR | NR |
| | TP | 3 | 3 | 2.5 | 2.5 | 2 | 1 | 1 | 1 | 0 | 0 | 2.5 | 2 | NR | NR | NR | NR | NR | NR | NR | NR |
| 19 | C | 3 | 3 | 3 | 3 | 3 | 3 | 3 | 3 | 3 | 2.5 | 2.5 | 2 | 2 | 1 | 1 | 1 | 0.5 | 0.5 | NR | NR |
| | TP | 2 | 2 | 2 | 1.5 | 1.5 | 0.5 | 0.5 | 0.5 | 0 | 1.5 | 1.5 | 1 | 0 | 0.5 | 0 | NR | NR | NR | NR | NR |
| 20 | C | 3 | 3 | 3 | 2 | 2 | 1 | 1 | 1 | 1 | 0 | 0 | 0 | 1 | 1 | 1 | 0.5 | 0.5 | 0 | NR | NR |
| | TP | 3 | 3 | 3 | 3 | 3 | 3 | 3 | 3 | 3 | 3 | 2.5 | 2 | 2 | 1 | 1 | 1 | 0.5 | 0.5 | NR | NR |
| 21 | C | 3 | 3 | 3 | 3 | 3 | 3 | 3 | 3 | 3 | 3 | 2.5 | NR | NR | NR | NR | NR | NR | NR | NR | NR |
| | TP | 3 | 3 | 3 | 2 | 2 | 1 | 1 | 1 | 1 | 0 | 0 | NR | NR | 1.5 | 1.5 | 1.5 | 1 | 1 | NR | NR |
| 22 | C | 3 | 2.5 | 2.5 | 3 | 3 | 3 | 3 | 3 | 3 | 3 | 2.5 | 2.5 | 2.5 | NR | NR | NR | NR | NR | NR | NR |
| | TP | 3 | 3 | 3 | 3 | 3 | 1 | 1 | 1 | 1 | 0.5 | 0 | 1 | 0 | 1 | 1 | 1 | 0.5 | 0.5 | NR | NR |
| 23 | C | 3 | 3 | 3 | 2.5 | 2.5 | 1.5 | 1.5 | 1.5 | 1.5 | 1.5 | 1 | 2.5 | 1 | 0 | 0 | 0 | 0.5 | 0.5 | NR | NR |
| | TP | 3 | 3 | 3 | 3 | 3 | 3 | 3 | 3 | 3 | 3 | 3 | 2 | 2.5 | 1 | 1 | 1 | 0.5 | 0.5 | NR | NR |
| 24 | C | 3 | 3 | 3 | 3 | 3 | 1 | 1 | 1 | 1 | 1 | 0.5 | 0 | 0.5 | 1 | 1 | 1 | 0.5 | 0.5 | NR | NR |
| | TP | 3 | 3 | 3 | 3 | 3 | 3 | 3 | 3 | 3 | 3 | 2.5 | 2 | 2.5 | 1 | 1 | 1 | 0.5 | 0.5 | NR | NR |
| 25 | C | 3 | 3 | 3 | 2.5 | 2.5 | 1 | 1 | 1 | 1 | 0.5 | 0 | 0 | 0 | 0.5 | 0.5 | 0.5 | 0 | 0 | NR | NR |
| | TP | 3 | 3 | 3 | 3 | 3 | 3 | 3 | 3 | 3 | 2.5 | 2.5 | 2 | 2.5 | 1 | 1 | 1 | 0.5 | 0.5 | NR | NR |
| 26 | C | 3 | 3 | 3 | 2.5 | 2.5 | 1 | 1 | 1 | 1 | 0 | 0 | 0 | 0 | 1 | 1 | 1 | 0.5 | 0.5 | NR | NR |
| | TP | 3 | 3 | 3 | 3 | 3 | 3 | 3 | 3 | 3 | 2.5 | 2 | 2 | 2 | 1 | 1 | 1 | 0.5 | 0.5 | NR | NR |
| 27 | C | 3 | 3 | 3 | 1.5 | 1.5 | 0 | 0.5 | 0.5 | 0.5 | 0 | NR | NR | NR | 1 | 1 | 1 | 0.5 | 0.5 | NR | NR |
| | TP | 3 | 3 | 3 | 3 | 3 | 2.5 | 2.5 | 2.5 | 2.5 | 2.5 | 2 | 1.5 | 2 | NR | NR | NR | NR | NR | NR | NR |
| 28 | C | 3 | 3 | 3 | 3 | 3 | 2.5 | 2.5 | 2.5 | 2.5 | 2.5 | 2 | 1.5 | 2 | 0.5 | 0.5 | 0.5 | 0 | 0 | NR | NR |

FIGURE 1 (CON)

| | | | | | | | | | | | | | | | | | | | | | | |
|---|---|---|---|---|---|---|---|---|---|---|---|---|---|---|---|---|---|---|---|---|---|---|
| 29 | TP | 3 | 3 | 3 | 3 | 2.5 | 2 | 1 | 1 | 1 | 1 | 0.5 | 0 | NR | NR | NR | NR | NR | NR | NR | NR | NR |
| | C | 3 | 3 | 3 | 3 | 3 | 3 | 3 | 3 | 3 | 3 | 3 | 2 | 1.5 | 1 | 1 | 1 | 0.5 | 0 | 0.5 | 0 | NR |
| 30 | TP | 3 | 3 | 3 | 3 | 2.5 | 2.5 | 1.5 | 1.5 | 1.5 | 1.5 | 1 | 0.5. | 0 | NR | NR | NR | NR | NR | NR | NR | NR |
| | C | 3 | 3 | 3 | 3 | 3 | 3 | 3 | 3 | 3 | 3 | 2.5 | 2.5 | 2 | 1.5 | 1 | 1 | 1 | 0.5 | 0.5 | NR | NR |
| 31 | TP | 3 | 3 | 3 | 3 | 3 | 2.5 | 1.5 | 1.5 | 1.5 | 1.5 | 1 | 0.5 | 0 | NR | NR | NR | NR | NR | NR | NR | NR |
| | C | 3 | 3 | 3 | 3 | 3 | 3 | 3 | 3 | 3 | 3 | 3 | 2.5 | 2 | 2 | 1 | 1 | 1 | 0.5 | 0 | NR | NR |
| 32 | TP | 3 | 3 | 3 | 3 | 2.5 | 2.5 | 1.5 | 1.5 | 1.5 | 1.5 | 1 | 0.5 | 0 | NR | NR | NR | NR | NR | NR | NR | NR |
| | C | 3 | 3 | 3 | 3 | 3 | 3 | 3 | 3 | 3 | 3 | 3 | 2.5 | 2.5 | 1.5 | 1.5 | 1.5 | 1 | 0.5 | 0 | NR | NR |
| 33 | TP | 3 | 3 | 3 | 2.5 | 2 | 2 | 1 | 1 | 1 | 1 | 0.5 | 0 | NR | NR | 0.5 | 0.5 | 0 | NR | NR | NR | NR |
| | C | 3 | 3 | 3 | 3 | 3 | 3 | 3 | 3 | 3 | 3 | 2.5 | 2 | 2 | 1.5 | 0.5 | 0.5 | NR | NR | NR | NR | NR |
| 34 | TP | 2.5 | DS | DS | DS | DS | DS | DS | DS | DS | DS | 1 | DS | DS | DS | DS | DS | DS | DS | DS | DS | DS |
| | C | 2.5 | DS | DS | DS | DS | DS | DS | DS | DS | DS | DS | DS | DS | DS | DS | DS | DS | DS | DS | DS | DS |
| 35 | TP | 3 | 3 | 2.5 | 3 | 2 | 2 | 1 | 1 | 1 | 1 | 0.5 | 0 | NR | NR | NR | NR | NR | NR | NR | NR | NR |
| | C | 3 | 3 | 3 | 3 | 3 | 3 | 3 | 3 | 3 | 3 | 2.5 | 2 | 2 | 1.5 | 0.5 | 0.5 | 0.5 | 0 | DS | DS | NR |

TP = Test Product site
C = Control site
NR = no readings taken; site evaluations completed
DS = Discontinued Subject

COMPOSITIONS FOR SKIN APPLICATION

CROSS-REFERENCE TO RELATED APPLICATIONS

The present application is a continuation of U.S. patent application Ser. No. 15/593,509, filed May 12, 2017, entitled COMPOSITION FOR SKIN APPLICATION, which application claims the benefit of U.S. Provisional Patent Application Ser. No. 62/335,918, filed May 13, 2016, entitled COMPOSITION FOR SKIN APPLICATION, the disclosures of both of which applications are incorporated by reference herein in their entireties for all purposes.

FIELD OF INVENTION

The present invention relates to the fields of skin care compositions, more specifically to preparations for application to the skin.

BACKGROUND OF THE INVENTION

Many compositions exist for application to the skin for various purposes including providing a sunscreen, softening, moisturizing, exfoliating, wrinkle removal, scar removal, repairing damage, anti-aging, or treating infection. The compositions described herein provide improved anti-aging and repair effects for skin.

SUMMARY OF THE INVENTION

A skin care composition is provided comprising *Thermus thermophilus* ferment and silybin. In some embodiments, the skin care composition comprises: from about 0.5 to about 5 percent by weight (wt %), of *Thermus thermophilus* ferment, and from about 0.05 to about 0.5 wt % of silybin, all weight percents based on the total weight of the composition.

In some embodiments, skin care composition further comprises one or more additional substances selected from carnosine, adenosine and CG-EDP3. In some embodiments, the skin care composition comprises: from 0 to about 0.5 wt % of carnosine, from 0 to about 0.1 wt % of adenosine, and from 0 to about 0.00015 of CG-EDP3, all weight percents based on the total weight of the composition.

In some embodiments, the skin care composition further comprises one or more substances selected from emulsifiers, humectants, lubricants, sufactants, dispersants, preservatives, moisturizers.

In some embodiments, the skin care composition further comprises a carrier. The carrier may be an aqueous carrier.

BRIEF DESCRIPTION OF THE DRAWINGS

For a more complete understanding of the present disclosure, reference is made to the following detailed description of exemplary embodiments considered in conjunction with the accompanying drawing.

FIG. 1 is a chart of control and test site evaluation results in accordance with an embodiment of the present disclosure.

DETAILED DESCRIPTION OF THE INVENTION

The skin care compositions contemplated herein comprise the substances *Thermus thermophilus* ferment and silybin. Optionally, the compositions contemplated and described herein further comprise one or more additional substances selected from carnosine, adenosine and CG-EDP3. The substances are dispersed in an aqueous carrier, such as water, to be applied to the skin in a spreadable form. The compositions comprising these substances provide anti-aging and reparative effects for skin. As is typical for compositions applicable to the skin, the compositions contemplated herein may further comprise any one or more of various emulsifiers, humectants, lubricants, sufactants, dispersants, preservatives, moisturizers, and other substances that will impart the desired functional and aesthetic properties to the compositions.

*Thermus thermophilus* ferment is a substance described in detail in US Patent Application Publication No. 2004/0115766, which incorporated herein by reference. More particularly, *Thermus thermophilus* ferment is a mixture of proteins obtained by fermentation of micro-organisms of the family *Thermus*, which can be found adjacent hydrothermal sources in deep marine environments. *Thermus thermophilus* ferment is commercially available, for example without limitation, under the tradename VENUCEANE™ from Sederma of Edison, N.J., U.S.A. or Le Perray en Yvelines cedex, France. It is believed that *Thermus thermophilus* ferment has a detoxifying and anti-radical effect and is useful for preventing and/or treating damage to skin associated with infrared radiation, such as spots, wrinkles and dryness resulting from exposure to sunlight.

Silybin is a plant lignin, i.e., a major flavonolignan, obtained from seeds of *Silybum marianum*, which is also known as the Mediterranean milk thistle. Silybin is commercially available from Puredia Corporation Ltd of Kowloon, Hong Kong. Silybin is also commercially available from Indena USA, Inc. of Seattle, Wash., USA. Silybin is also commercially available from Provital, S.A. of Barcelona, Spain, as well as from Orient Stars LLC of Carson, Calif., USA. It is believed that silybin and its related silymarins, also known as flavonolignins (e.g., silybum, silybinin, silydianin, silychristin, siosilybin), may be useful as cross-linking, anti-inflammatory, anti-wrinkle, moisturizing agents, as well as promoting collagen production in the skin and resisting ultraviolet injury to the skin.

Carnosine is a dipeptide of the amino acids beta-alanine and histidine and is found primarily in muscle and brain tissues. Carnosine is commercially available from Kumar Organic Products Ltd. Of Bangalore, India. Carnosine is also commercially available from Symrise of Teterboro, N.J., USA. Carnosine is also commercially available from Orient Stars LLC of Carson, Calif., USA. It is believed that carnosine is useful for skin whitening and moisturizing, as well as freckle reduction.

Adenosine is a purine nucleoside comprising a molecule of adenine attached to a ribose sugar molecule moiety. Adenosine is commercially available from Orient Stars LLC of Carson, Calif., USA. Adenosine is also commercially available from Spectrum Manufacturing of New Brunswick, N.J., USA. Adenosine is believed to be an anti-aging and anti-oxidation agent for skin.

CG-EDP3 generally comprises a blend of disodium ethylenediaminetetraacetic acid (EDTA), glycerin, *Glycine soja* (soybean) oil, hydrogenated lecithin, oligopeptide-24, phenoxyethanol, and sodium oleate in water. CG-EDP3 is a tradename and is commercially from Caregen of Gunpo-si, South Korea. It is believed that CG-EDP3 is useful for regeneration of damaged skin and providing anti-aging effects.

More particularly, skin care compositions according to the embodiments contemplated herein comprise the aforesaid substances in the amounts provided in Table 1 below.

TABLE 1

| Compound | % by Weight |
|---|---|
| Thermus thermophilus ferment | 0.5-5 |
| silybin | 0.05-0.5 |
| carnosine | 0-0.5 |
| adenosine | 0-0.1 |
| CG-EDP3 | 0-0.00015 |

As indicated in Table 1, the *Thermus thermophilus* ferment is included in the composition in an amount of from about 0.5 to about 5 percent (%), by weight, based on the total weight of the composition. In some embodiments, for example without limitation, the composition comprises from about 1 to about 3% of *Thermus thermophilus* ferment, or from about 1 to about 2, or from about 1.4 to about 1.6%, by weight, based on the total weight of the composition.

As also indicated in Table 1, the silybin is included in the composition in an amount of from about 0.05 to about 0.5%, by weight, based on the total weight of the composition. In some embodiments, for example without limitation, the composition comprises from about 0.1 to about 0.3% of silybin, or from about 0.1 to about 0.2, or from about 0.10 to about 0.15%, by weight, based on the total weight of the composition.

The compositions contemplated herein may, optionally, further comprise from 0 to about 0.5% of carnosine, by weight, based on the total weight of the composition. In some embodiments, for example without limitation, the composition comprises from about 0.01 to about 0.5% of carnosine, or from about 0.05 to about 0.4%, or from about 0.1 to about 0.3%, by weight, based on the total weight of the composition.

The compositions contemplated herein may, optionally, further comprise from 0 to about 0.1% of adenosine, by weight, based on the total weight of the composition. In some embodiments, for example without limitation, the composition comprises from about 0.01 to about 0.08% of adenosine, or from about 0.02 to about 0.7%, or from about 0.03 to about 0.05%, by weight, based on the total weight of the composition.

The compositions contemplated herein may, optionally, further comprise from 0 to about 0.00015% of CG-EDP3, by weight, based on the total weight of the composition. In some embodiments, for example without limitation, the composition comprises from about 0.00005 to about 0.00015% of CG-EDP3, or from about 0.000075 to about 0.000125%, or from about 0.0001 to about 0.000125%, by weight, based on the total weight of the composition.

The compositions contemplated herein may further comprise a carrier which may be aqueous or non-aqueous. In one embodiment, an aqueous carrier comprises for example, without limitation, from about 30 to about 100% of water, by weight, based on the total weight of the carrier. A non-aqueous carrier may, for example without limitation, comprise from about 30 to about 100% of an organic liquid or gel, such as glycerol or another alcohol. The substances are dispersed in the carrier to be applied to the skin in a spreadable form (e.g., a lotion, gel or cream).

In some embodiments, other substances are added to the skincare composition to improve its aesthetic qualities or promote skin health or healing. For example, without limitation, carriers, emulsifiers, humectants, lubricants, surfactants, thickeners, preservatives, moisturizers, and other additives may be included in the composition with one or more of the substances discussed hereinabove (i.e., *Thermus thermophilus* ferment, silybin, carnosine, adenosine and CG-EDP3). Suitable emulsifiers include, without limitation, sorbitan monostearate, lecithin, and potassium phosphate. Suitable humectants include, without limitation, propylene glycol, propandiol, and glycerin. Suitable lubricants include, without limitation, glycerin, dimethicone and glyceryl oleate. Suitable surfactants include, without limitation, polyethylene glycol-100 stearate, glyceryl stearate, and potassium cetyl phosphate. Suitable thickeners include, without limitation, $C_{12}$-$C_{15}$ alkyl benzoate, carbomer and xantham gum. Suitable preservatives include, without limitation, potassium sorbate, phenoxyethanol, and chlorphenisin. Suitable moisturizers include, without limitation, dimethicone, caprylic or capric triglyceride, and capryl methicone.

The exemplary compositions are easily and smoothly applied to the skin and provide improved anti-aging and reparative activity to the skin where applied. The exemplary compositions are expected to be non-irritating and soothing in normal use. Depending on the other substances that are included in the exemplary compositions, as will be readily understood by persons of ordinary skill in the relevant art, the compositions contemplated and described herein are useful for many purposes relating to skin care and repair, including without limitation, sunscreen, softening, moisturizing, exfoliating, wrinkle removal, scar removal, repairing damage, anti-aging, or treating infection.

EXAMPLES

Example 1

A. Components of Test Product

Formulation of a sample composition ("Test Product") for application to the skin as a sunscreen, containing the substances listed in Table 2 below, will now be described.

TABLE 2

| # | Phase | Ingredients | Quantity (w/w %) |
|---|---|---|---|
| 1 | A | WATER (AQUA) | 51.41287 |
| 2 | C | CAPRYLYL METHICONE | 4.000000 |
| 3 | B | DIPROPYLENE GLYCOL | 4.000000 |
| 4 | C | DICAPRYLYL CARBONATE | 3.000000 |
| 5 | A2 | PEG/PPG-17/6 COPOLYMER | 2.000000 |
| 6 | A3 | POTASSIUM CETYL PHOSPHATE | 1.562500 |
| 7 | G | *THERMUS THERMOPHILUS* FERMENT | 1.408500 |
| 8 | C | GLYCERYL STEARATE | 1.250000 |
| 9 | C | POLYETHYLENE GLYCOL-100 STEARATE | 1.250000 |
| 10 | C | METHYL GLUCOSE SESQUISTEARATE | 1.000000 |
| 11 | G | SD ALCOHOL 40-B (from Pride Solvents of Avenel, New Jersey) | 1.000000 |

TABLE 2-continued

| # | Phase | Ingredients | Quantity (w/w %) |
|---|---|---|---|
| 12 | A1 | ACRYLATES/C10-30 ALKYL ACRYLATE CROSSPOLYMER | 0.200000 |
| 13 | A2 | ADENOSINE | 0.400000 |
| 14 | E | C11-15 PARETH-40 | 0.050000 |
| 15 | E | C11-15 PARETH-7 | 0.050000 |
| 16 | E | CAPRYLYL GLYCOL | 0.360000 |
| 17 | H | CARNOSINE | 0.200000 |
| 18 | C | CETYL ALCOHOL | 0.600000 |
| 19 | A2 | DIPOTASSIUM GLYCYRRHIZATE | 0.050000 |
| 20a | A2 | DISODIUM EDTA | 0.200000 |
| 20b | C | DISODIUM EDTA | 0.020000 |
| 21 | E | DISODIUM LAURYL SULFOSUCCINATE | 0.010000 |
| 22 | I | FRAGRANCE | 0.050000 |
| 23 | G | GLYCERIN | 0.275001 |
| 24 | G | *GLYCINE SOJA* (SOYBEAN) OIL | 0.000000 |
| 25 | G | HEXYLENE GLYCOL | 0.060000 |
| 26 | G | HYDROGENATED LECITHIN | 0.000000 |
| 27 | A3 | HYDROGENATED PALM GLYCERIDES | 0.937500 |
| 28 | F | ISOHEXADECANE | 0.450000 |
| 29 | B | LECITHIN | 0.180000 |
| 30 | G | OLIGOPEPTIDE-24 | 0.000000 |
| 31 | A2 | PANTHENOL | 0.400000 |
| 32 | C | POLYETHYLENE GLYCOL-10 DIMETHICONE | 0.300000 |
| 33a | E | PHENOXYETHANOL | 0.050000 |
| 33b | G | PHENOXYETHANOL | 0.395001 |
| 34 | E | POLYACRYLATE-15 | 0.350000 |
| 35 | E | POLYACRYLATE-17 | 0.150000 |
| 36 | G | POLYGONUM AVICULARE EXTRACT | 0.180000 |
| 37 | F | POLYSORBATE 80 | 0.150000 |
| 38 | D | POTASSIUM HYDROXIDE | 0.072625 |
| 39 | G | POTASSIUM SORBATE | 0.128000 |
| 40 | B | SILYBIN | 0.120000 |
| 41 | F | SODIUM ACRYLATE/SODIUM ACRYLOYLDIMETHYL TAURATE COPOLYMER | 0.750000 |
| 42 | G | SODIUM BENZOATE | 0.018000 |
| 43 | E | SODIUM LAURETH-12 SULFATE | 0.010000 |
| 44 | G | SODIUM OLEATE | 0.000000 |
| 45 | F | SORBITAN OLEATE | 0.050000 |
| 46 | C | TOCOPHERYL ACETATE | 0.300000 |
| 47 | C | HOMOSALATE (HOMOMENTHYL SALICYLATE) | 10.000000 |
| 48 | C | ETHYLHEXYL SALICYLATE (OCTISALATE) | 5.000000 |
| 49 | C | BUTYL METHOXYDIBENZOYLMETHANE (AVOBENZONE) | 3.000000 |
| 50 | C | OCTOCRYLENE | 2.600000 |
| | | TOTAL | 100.000000 |

All ingredients are provided and combined as described below in amounts calculated to provide the weight percentage of the Test Product as reported in Table 2, which is based on the total weight of the Test Product.

Premix A

A large portion of cold deionized water is placed into a tank, with smaller portions held back to prepare Premix B, Premix C, Premix D and Premix H. Fast mixing is commenced to create a vortex and the Phase A1 substance (acrylates/$C_{10-30}$ alkyl acrylate crosspolymer, #12) is slowly sprinkled into the tank with the water. During continuous mixing, the following Phase A2 substances are added to the tank: dipotassium glycyrrhizate (#19), adenosine (#13), disodium ethylenediaminetetraacetic acid (EDTA) (#20a), panthenol (#31), and PEG/PPG-17/6 copolymer (#5). Mixing is continued for 20 to 30 minutes, adjusting mixer speed as mixture thickens, until fully hydrated and uniform with no fish eyes. Heating to 80° C.-82° C. is commenced and mixing continues for 10 to 15 minutes until the mixture is uniform. The main tank with Premix A is covered and set aside.

Phase B

A small portion of water (#1) and all of the Phase B substances, silybin (#40), lecithin (#29) and dipropylene glycol (#3), are added to a stockpot and heated to 60° C.-65° C. while stirring with a mixer, for 5 to 10 minutes until uniform. The stockpot with Premix B is covered and set aside.

Premix C

A small portion of water (#1) and the Phase C substances are placed into a tank, heated to 80° C.-82° C., and stirred at slow to medium speed for 5 to 10 minutes until uniform. Phase C substances include: glyceryl stearate (#8), polyethylene glycol-100 stearate (#9), methyl glucose sesquistearate (#10), cetyl alcohol (#18), homosalate (#47), octocrylene (#50), butyl methoxydibenzoylmethane (#49), ethylhexyl salicylate (#48), disodium EDTA (#20b), dicaprylyl carbonate (#4), tocopheryl acetate (#46), polyethylene glycol dimethicone (#32) and caprylyl methicone (#2). The Phase C mixture is heated to 80° C.-82° C. while mixing on slow to medium mixing speed for 5 to 10 minutes, until uniform. The tank with Premix C is covered and set aside.

Premix D

A small portion of water (#1) and is added to a stockpot and, while stirring, potassium hydroxide (#38) is slowly added to the water in the stockpot. Premix D is stirred, for 5 to 10 minutes until the potassium hydroxide is dissolved and uniformly mixed, and then covered and set aside.

Premix H

A small portion of water (#1) and the Group H substance, carnosine (#17) are added to a stockpot and stirred for 5-10 minutes until completely dispersed. The stockpot with Phase H mixture is covered and set aside.

Main Tank

The Premix A is added to a main tank, heated to 80° C.-82° C. and mixed. Then the Phase A3 substances, hydrogenated palm glycerides (#27) and potassium cetyl phosphate (#6), are added to the tank and mixed for 10 to 15 minutes until uniform. The Phase A mixture is cooled to 73° C.-75° C., while Premix B is reheated to 60° C.-65° C., if necessary. When both Premix A and Premix B reach the aforesaid temperatures, Premix B is added to Premix A in the main tank, while continuing to mix for another 5 to 10 minutes until uniform. The main tank and its contents are held at 73° C.-75° C.

Premix C is reheated to 80° C.-82° C., if necessary, and then added to the main tank, while stirring continues.

The contents of the main tank (i.e., Premixes A, B and C) are homogenized for 5 to 8 minutes. Premix D is then added to the main tank while homogenation mixing continues for another 3 to 5 minutes.

The Phase E substances are then added to the main tank while homogenation mixing continues for another 3 to 5 minutes. The Phase E substances include $C_{11-15}$ Pareth-40 (#14), $C_{11-15}$ Pareth-7 (#15), caprylyl glycol (#16), disodium lauryl sulfosuccinate (#21), phenoxyethanol (#33a), polyacrylate-15 (#34), polyacrylate-17 (#35), and sodium laureth-12 sulfate (#43).

Homogenation mixing is ceased and the main tank and its contents are cooled to 60° C.-63° C. The Phase F substances are premixed with one another. The Phase F substances include: isohexadecane (#28), polysorbate 80 (#37), sodium acrylate/sodium acryloyldimethyl taurate copolymer (#41), and sorbitan oleate (#45). After the main tank reaches the cooled temperature, the Phase F premix is added to the main tank and the mixture homogenized for 5 to 8 minutes.

The main tank and its contents are cooled to 43° C.-45° C. and then, with continued stirring, the Group G substances were added: caprylyl glycol (#16), hexylene glycol (#25), phenoxyethanol (#33b), potassium sorbate (#39), SD Alcohol 40-B (#11), glycerin (#23), polygonum aviculare extract (#36), sodium benzoate (#42), *Thermus thermophilus* ferment (#7), oligopeptide-24 (#30), *Glycine soja* (soybean) oil (#24), and sodium oleate (#44).

Premix H (containing carnosine) is added to the main tank next, followed by the Phase I substance, Warm Sandalwood (#34), while stirring continues. The contents of the main tank are mixed for another 15 to 20 minutes until uniform and then cooled to 28° C.-30° C. Upon reaching the cooled temperature, the mixing is ceased.

B. Performance of Test Product

A study was performed using the Test Product formulated in Part A above on human subjects to test performance. More specifically, the study was designed to determine whether skin cell turnover (i.e., exfoliation) at skin sites treated with the Test Product was increased or improved compared to untreated sites.

Dansyl chloride, a fluorescent blue- or blue-green substance was used at the untreated and treated skin sites to provide a means for measuring cell turnover at those sites. The dye fades as skin cells are lost from the surface of the skin during cell turnover. The faster the dye fades, the faster the cell turnover is occurring, and the faster skin regeneration is occurring.

35 human test subjects were initially enlisted for this study and randomly assigned a subject number of 1-35. There were 9 males, 26 females and a mix of ethnicities. 34 of the test subjects successfully completed the study. One test subject dropped out of the study for reasons unrelated to the study.

All test subjects had dansyl chloride applied to a control test site on their upper arms by a trained individual. The dansyl chloride control sites remained otherwise untreated throughout the duration of the study.

All evenly numbered test subjects also had dansyl chloride applied to a test site on their upper left arm. All oddly-numbered test subjects had dansyl chloride applied to a test site on their upper right arm. The Test Product was applied to the test site on each test subject, in 0.2 gram amounts. More particularly, each enrolled human subject had the Test Product applied by a trained clinical technician every weekday morning using a finger cot. The test subjects each applied the Test Product to the test site at home in the evening using a finger cot. There was no Test Product application on Saturday or Sunday. The volume of Test Product applied to the test site was sufficient to cover the area when rubbed in with the finger using a finger cot for approximately 10 scrubs.

Each enrolled test subject was provided with instructions on washing of the test site. Washing of the test sites during the course of the study was done using Ivory Soap® provided by the testing facility.

Each day of the study, both the control and the test sites were evaluated visually for intensity of the dansyl chloride staining and assigned a value based on the following visual assessment scale and the results are provided in FIG. 1.

Intensity of Dansyl Chloride Stain:

0=No stain (except for fine hairs or follicles)

0.5=Barely perceptible evidence of stain (with or without more intense hair or follicle staining)

1=Partial or light stain (with or without more intense hair or follicle staining)

2=Moderate stain covering all of contact area (with or without more intense hair or follicle staining)

3=Intense, fully stained area (Intermediate scores of 1.5 and 2.5 were utilized when necessary)

The study continued until no dansyl chloride stain was visible on any site with UV-light examination (Model B0100A Black-Ray Long Wave UV from Ultra-violet Products, Inc., San Gabriel, Calif., USA). When no dansyl chloride stain is discernable upon UV-light examination (i.e., when the intensity score above is 0) that is considered to be 100% cell turnover and is referred to as the point of extinction.

A decrease in dansyl chloride stain intensity compared with the control site was observed for all test subject on Days 2-17 of the study. Overall, the test site treated with the Test Product was associated with a faster cell turnover than that observed on the control site on Days 2-17. The difference from the control site was statistically significant on Days 3-12.

A comparison of the mean time until extinction was made between the test site and the control site using a paired difference t-test. The mean time to extinction (mean+/− standard error) are summarized below:

Test Site: 10.2+/−0.2

Control Site: 16.5+/−0.3

It will be understood by those having ordinary skill in the art and possession of the present disclosure that the embodiments described herein are merely exemplary in nature and that a person skilled in the art may make many variations and modifications thereto without departing from the scope of the present invention. All such variations and modifications, are intended to be included within the scope of the invention.

We claim:

1. A skin care composition comprising:
   from about 0.5 to about 5 percent by weight (wt %), of *Thermus thermophilus* ferment, and
   from about 0.05 to about 0.5 wt % of silybin, all weight percents based on the total weight of the composition.

2. The skin care composition of claim 1, further comprising one or more substances selected from emulsifiers, humectants, lubricants, surfactants, dispersants, preservatives, moisturizers.

3. The skin care composition of claim 1, further comprising a carrier.

4. The skin care composition of claim 3, wherein the carrier is an aqueous carrier.

5. The skin care composition of claim 1, further comprising one or more additional substances selected from carnosine, adenosine and CG-EDP3.

6. The skin care composition of claim 5, comprising:
   from 0 to about 0.5 wt % of carnosine,
   from 0 to about 0.1 wt % of adenosine, and
   from 0 to about 0.00015 of CG-EDP3, all weight percents based on the total weight of the composition.

7. The skin care composition of claim 5, further comprising a carrier.

8. The skin care composition of claim 7, wherein the carrier is an aqueous carrier.

9. The skin care composition of claim 5, further comprising one or more substances selected from emulsifiers, humectants, lubricants, surfactants, dispersants, preservatives, moisturizers.

10. The skin composition of claim 1, comprising from about 1 to about 2 wt % of *Thermus thermophilus* ferment.

11. The skin composition of claim 1, comprising from about 0.1 to about 0.2 wt % of silybin.

12. The skin care composition of claim 6, comprising from about 0.05 to about 0.4 wt % of carnosine.

13. The skin care composition of claim 6, comprising from about 0.02 to about 0.7 wt % of adenosine.

14. The skin composition of claim 6, comprising from about 0.000075 to about 0.000125 wt % of CG EDP3.

* * * * *